United States Patent [19]

Harrison et al.

[11] Patent Number: 5,530,424
[45] Date of Patent: *Jun. 25, 1996

[54] APPARATUS AND METHOD FOR HIGH DATA RATE COMMUNICATION IN A COMPUTERIZED TOMOGRAPHY SYSTEM

[75] Inventors: Daniel D. Harrison; Richard L. Frey, both of Delanson, N.Y.

[73] Assignee: General Electric Company, Schenectady, N.Y.

[*] Notice: The term of this patent shall not extend beyond the expiration date of Pat. No. 5,530,7220.

[21] Appl. No.: 307,120

[22] Filed: Sep. 16, 1994

[51] Int. Cl.⁶ .................................................. A61B 6/00
[52] U.S. Cl. ............................. 340/500; 378/4; 378/15
[58] Field of Search ............................. 340/540, 539, 340/671, 500; 455/66, 67.1; 333/109, 116, 243; 343/700 MS; 378/4, 15, 98; 364/413.14, 413.15; 250/370.08, 370.09

[56] References Cited

U.S. PATENT DOCUMENTS

| 4,651,338 | 3/1987 | Hahn | 378/15 X |
| 5,140,696 | 8/1992 | Fox | 378/15 X |
| 5,157,393 | 10/1992 | Fox et al. | 378/15 X |
| 5,208,581 | 5/1993 | Collins | 378/4 X |
| 5,229,871 | 7/1993 | Czarnek et al. | 359/15 |
| 5,287,117 | 2/1994 | Posluszny | 378/15 X |

Primary Examiner—Thomas Mullen
Attorney, Agent, or Firm—Marvin Snyder

[57] ABSTRACT

Apparatus comprising a transmission line and a coupler are provided for high data rate communication between rotating and stationary frames of a computerized tomography system. The transmission line comprises individual segments each having a respective first end and a respective second end and having a respective electrical length chosen so that a modulated signal simultaneously applied at each respective first end has a predetermined time-delay upon arrival at each respective second end. The individual segments are arranged so that respective first ends of any two consecutive segments are substantially adjacent to one another and respective second ends of any two consecutive segments are substantially adjacent to one another to avoid time-delay discontinuity in the modulated signal propagating therethrough. The coupler is attached to the stationary frame and is sufficiently near the transmission line for establishing radio coupling therebetween so as to receive the modulated signal being applied to the respective individual segments.

44 Claims, 4 Drawing Sheets

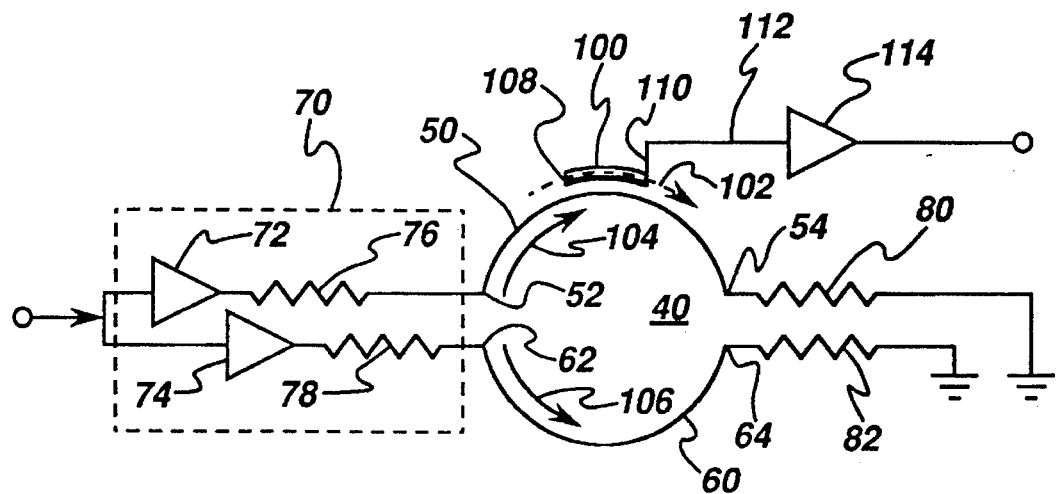
fig. 2
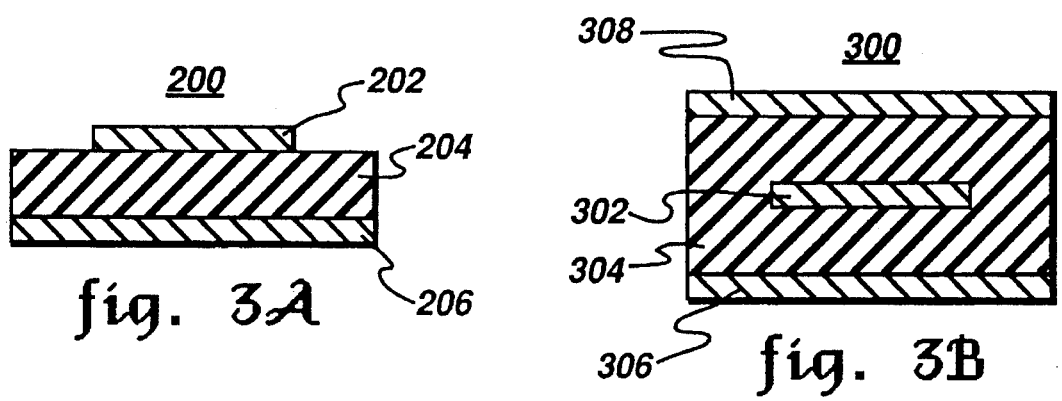
fig. 3A
fig. 3B
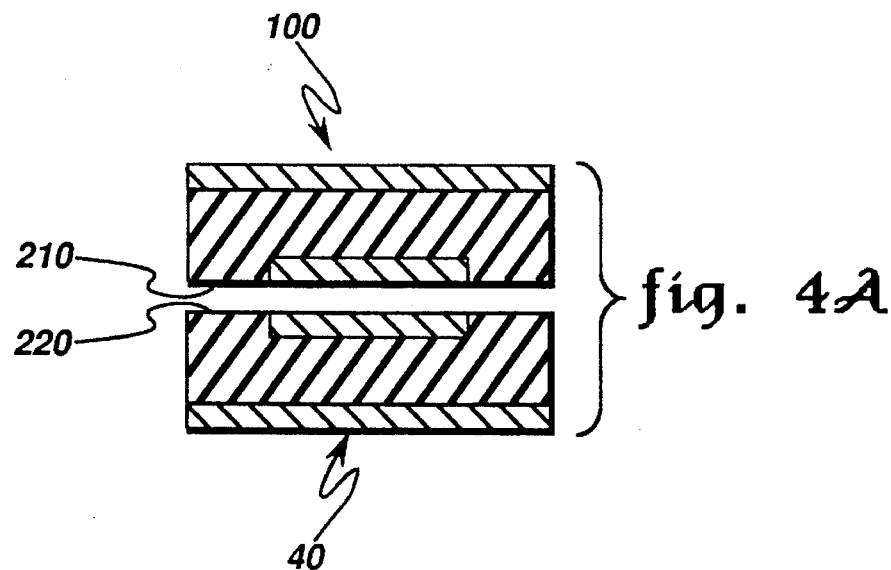
fig. 4A

APPARATUS AND METHOD FOR HIGH DATA RATE COMMUNICATION IN A COMPUTERIZED TOMOGRAPHY SYSTEM

RELATED APPLICATIONS

This application is related to patent application Ser. No. 08/307,118 by D. D. Harrison, entitled "Differentially Driven Transmission Line for High Data Rate Communication in a Computerized Tomography System", filed on Sep. 16, 1994; patent application Ser. No. 08/307,130 by D. D. Harrison, entitled "Radiation Shielded Apparatus for High Data Rate Communication in a Computerized Tomography System", filed on Sep. 16, 1994; and patent application Ser. No. 08/307,119 by D. D. Harrison, entitled "A Transmission Line With a Grounding Brush for High Data Rate Communication in a Computerized Tomography System", filed on Sep. 16, 1994. Each of the above listed patent applications is assigned to the assignee of the present invention and is herein incorporated by reference.

BACKGROUND OF THE INVENTION

The field of the present invention is generally related to computerized tomography (CT) and, particularly, to apparatus for high data rate communication in a CT system.

CT systems typically employ a rotating frame or gantry to obtain multiple x-ray images, or views, at different rotational angles. Each set of images is referred to in the art as a "slice". A patient or inanimate object is generally positioned in a central opening of the rotating frame on a table which is movable axially, thus enabling respective slices to be obtained at multiple axial positions as well. Each of the slices obtained is then processed in a computer according to predetermined algorithms to produce enhanced images for diagnostic or inspection purposes.

The rotating frame includes an x-ray source, a detector array and electronics necessary to generate image data for each view. A set of stationary electronics is employed for processing raw image data into the enhanced form. Thus, it is necessary to provide for communication of the image data between the rotating frame and a stationary frame of the CT system.

The data rate for communication between the stationary and rotating frames is an important factor because it is desirable to obtain the desired views as fast as possible to reduce patient discomfort and/or to maximize equipment utilization. In current CT systems, a single view typically comprises about 800 detector channels with a 16 bit representation for each individual detector channel output (i.e., 12.8 Kbits per view) and is typically repeated 1,000 times per second, yielding a net data rate requirement of approximately 13 Megabits per second (Mbit/sec) for image data alone. Future CT systems capable of simultaneously constructing multiple image slices by employing four, eight, or sixteen times as many detector channels will increase the data rate requirement to beyond 150 Mbit/sec for image data alone.

In order to provide a communications link with the requisite data rate, some prior CT systems have employed an umbilical cable connected to the rotating gantry. One or more flexible, shielded coaxial cables are used in the umbilical cable for high speed communications, and other conductors are used for power and discrete control signals. The umbilical cable is typically capable of plus or minus 360° of rotation, so that the gantry is limited, for example, to a total of 720° of rotation. In operation, the gantry is accelerated to a desired rotational speed and the desired views are taken before the 720° limit is reached. Near the 720° limit, the gantry is decelerated to a stop, and then accelerated in the reverse direction to acquire more views. The gantry thus cycles back and forth within the 720° limit.

Such "cycling" type CT systems have two main disadvantages. One disadvantage is that the decelerating and re-accelerating of the gantry is fairly time consuming. The gantry, with all equipment in place, is both large and massive, so that even with large motors, the time consumed in accelerating the gantry can be substantial. The second disadvantage is somewhat of a corollary to the first, in that the need to repeatedly accelerate such a large mass produces a large amount of mechanical stress and wear.

Another type of CT system is known in the art in which brushes and slip rings are utilized for electrically linking the rotating frame to the stationary frame. In these systems, the rotating frame or gantry is free to rotate continuously, eliminating the need for the above described back-and-forth movement of the gantry and thereby providing greater flexibility for the acquisition of the desired views. However, prior CT systems utilizing brushes and slip rings for communications have generally suffered from significant limitations in the data rates which can be achieved. This is due to the substantial time required to propagate the signals around the circular slip rings. At the desired data rates, the electrical path length around the rings is an appreciable fraction of a bit period, so that electromagnetic waves propagating around the rings in opposite directions may arrive at a reception point at substantially different times in a bit period, causing garbled reception.

U.S. Pat. No. 5,208,581 issued to A. K. Collins, assigned to the assignee of the present invention and herein incorporated by reference, is another type of gantry in which brushes and slip rings are employed for communication. Although the design of Collins provides relatively high speed communication between the stationary and rotating frames, the fact remains that the use of contacting brushes and rings inherently carries certain disadvantages. For example, the mechanical contact between the brushes and rings causes wear which requires such brushes and rings to be periodically replaced in order to maintain reliable communication. Furthermore, the design of Collins does not support the higher data rates needed for multiple-slice CT systems.

Other CT systems have employed an optical data link for communication between the stationary and rotating frames. Although an optical data link design avoids typical drawbacks of slip rings and brushes, such optical design requires optics which must be fabricated under tight specifications and which in operation require substantial spatial alignment in order to achieve reliable optical coupling along the relatively long circumference of the rotating frame. This leads to high costs and, thus, it is desirable to provide in a CT system an improved communication link which at a low cost provides reliable high data rate communication between the stationary and rotating frames of the CT system.

SUMMARY OF THE INVENTION

Generally speaking, the present invention fulfills the foregoing needs by providing in a computerized tomography (CT) system having a stationary frame and a generally annular rotating frame, an apparatus comprising a transmission line attached to the rotating frame and positioned around the rotating frame. The transmission line comprises individual segments each having a respective first end and a respective second end and having a respective electrical length chosen so that a modulated signal simultaneously applied at each respective first end has a predetermined time-delay upon arrival at each respective second end. The individual segments are arranged so that respective first ends of any two consecutive segments are substantially adjacent to one another and respective second ends of any two consecutive segments are substantially adjacent to one another to avoid time-delay discontinuity in the modulated signal propagating therethrough. The apparatus further comprises a coupler attached to the stationary frame and being sufficiently near the transmission line for establishing radio coupling therebetween so as to receive the modulated signal being applied to the respective individual segments.

A method for providing relatively high data rate communication between the stationary frame and the rotating frame comprises the following steps: attaching a transmission line comprising individual segments positioned around the rotating frame and wherein each individual segment has respective first and second ends; selecting the electrical length of each of the individual segments so that a modulated signal simultaneously applied at each respective first end has a predetermined time-delay upon arrival at each respective second end; arranging the individual segments so that respective first end of any two consecutive segments are substantially adjacent to one another and respective second ends of any two consecutive segments are substantially adjacent to one another to avoid time-delay discontinuity in the modulated signal propagating therethrough; attaching a coupler to the stationary frame; and positioning the coupler sufficiently near the transmission line for establishing radio coupling therebetween so as to receive the modulating signal being applied to the respective individual segments.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description in conjunction with the accompanying drawings in which like numbers represent like parts throughout the drawings, and in which:

FIG. 2 is an exemplary schematic representation of an apparatus employing a transmission line and a coupler in accordance with the present invention;

FIGS. 3A and 3B are respective cross sections of a microstrip and a stripline which can be utilized for the transmission line and/or coupler in respective exemplary embodiments for the apparatus of FIG. 2;

FIGS. 4A, 4B and 4C are respective cross sectional views showing exemplary arrangements of the transmission line and coupler shown in the apparatus of FIG. 2;

DETAILED DESCRIPTION OF THE INVENTION

Figure 1:
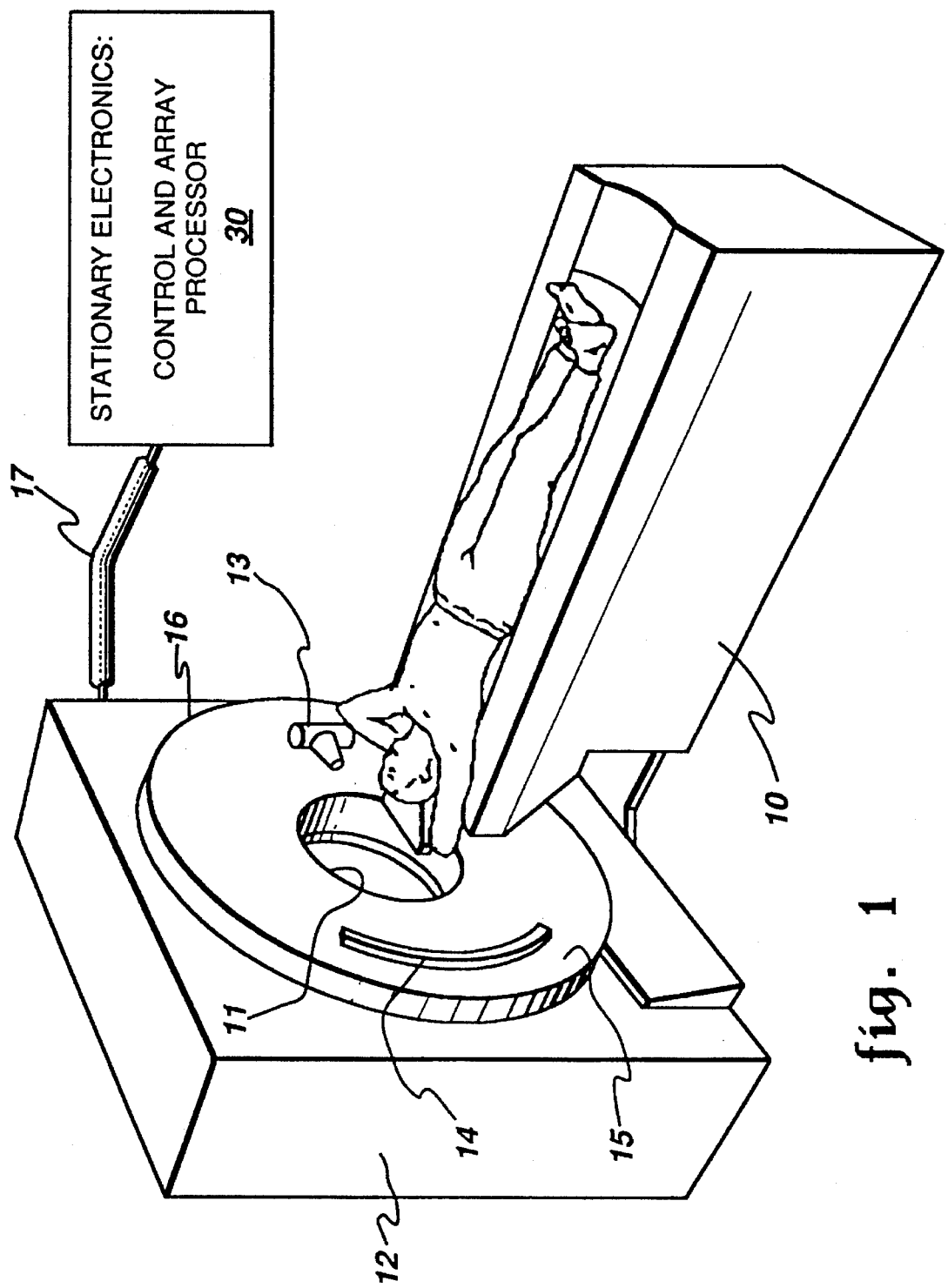
FIG. 1 is a perspective view of a CT system which employs the present invention.

As shown in FIG. 1, a CT system used to produce images of at least a region of interest of the human anatomy has a patient table 10 which can be positioned within the aperture 11 of a generally annular rotating frame or gantry 15 having a predetermined circumference, e.g., outer circumference 16. A stationary frame 12 is conveniently employed to support rotating frame 15. A source of imaging energy 13 which preferably produces highly collimated x-rays is mounted on the rotating frame to one side of its aperture 11, and a detector array 14 is mounted to the other side of the aperture. The rotating frame, together with x-ray source 13 and detector array 14, is revolved about the aperture during a scan of the patient to obtain x-ray attenuation measurements from many different angles through a range of at least 180° of revolution. Detector array 14 may comprise multiple rows each having about 800 detector channels along its length. The individual outputs of each channel in detector array 14 is connected to a data acquisition system, DAS (not shown). When sampled, each channel output is converted by the DAS to, for example, a 16 bit digital value representing X-ray intensity.

The rotating frame further includes additional onboard electronics (not shown) which rotates along with rotating frame 15. The onboard electronics is essentially a slave to stationary electronics systems 30 which is located off rotating frame 15. Stationary electronics systems 30 is a computer-based system for issuing commands to the onboard electronics on rotating frame 15 and for receiving the resulting image data, via suitable electrical leads 17 from stationary frame 12, to perform processing of the received image data.

The present invention is directed to an apparatus for high data rate communication between the rotating frame and the stationary frame through the use of a transmission line and a coupler or probe which advantageously avoid the use of slip rings and brushes and which allow for continuous rotation of rotating frame 15. As discussed above, multiple-slice CT systems require high data rate communication. The present invention advantageously allows for such high data rate communication, (e.g., exceeding 150 Mbits/sec.) without the use of brushes and slip rings or without the use of costly optical devices. Further, the present invention allows for reliable and cost effective high data rate communication notwithstanding the relatively long circumference (approximately 13 ft) of the rotating frame.

In the discussion which follows, it is assumed by way of example and not of limitation that all of the communication between rotating frame 15 and stationary frame 12 has been serialized, i.e., converted from parallel to serial data for transmission and viceversa on reception, employing well known multiplexing techniques. This is done so that only a single bit stream need be transmitted, although it should be apparent to those skilled in the art that multiple parallel paths according to the present invention could be employed. In each case, multilevel or multiphase encoding techniques can be employed to further increase the maximum data rate available.

As shown in FIG. 2, a transmission line 40 is attached to rotating frame 15 (FIG. 1) and can be positioned substantially around the rotating frame, for example, around the circumference of the rotating frame. Similarly, the transmission line can be conveniently affixed to the annulus of the rotating frame, i.e., the surface bounded by the concentric circles in the rotating frame; for example, the concentric circle which defines aperture 11 and the larger concentric circle which has circumference 16. Further, it will be appreciated that the present invention need not be limited to circular geometric arrangements since arrangements other than circular can equally benefit from the present invention.

Transmission line 40 comprises respective individual segments 50 and 60 each having a respective first end 52 and 62 and a respective second end 54 and 64. Each individual segment 50 and 60 has a respective electrical length chosen so that a modulated signal applied at each respective first end 52 and 62 has a predetermined time-delay upon arrival at each respective second end 54 and 64. It will be appreciated that if the respective electrical lengths for segments 50 and 60 are substantially similar to one another, the above-described segment arrangement results in the modulated signal arriving at each respective second end having a substantially similar time delay relative to one another.

The modulated signal, which can be conveniently supplied by the onboard electronics on rotating frame 15 employing any of a number of readily available modulation techniques such as frequency-shift keying and the like, can be readily split and amplified by a suitable driving circuit 70 comprising amplifiers 72 and 74 and optional matching resistors 76 and 78 having a predetermined resistance value selected to match the impedance characteristics of the respective transmission line segments. It will be apparent to those skilled in the art that other broad band impedance matching schemes can be effectively employed at the modulated signal source. Similarly, each respective second end 54 and 64 is respectively connected to termination resistors 80 and 82 having a predetermined resistance value chosen to minimize reflection of energy in individual transmission line segments 50 and 60. Other schemes may be employed which tolerate a predetermined time delay depending on the specific application. For example, amplifier 74 and matching resistor 78 could be connected to second end 64 in lieu of first end 62 and termination resistor connected to first end 62 in lieu of second end 64. In this case although a predetermined time delay would exist between respective first and second ends, such delay could be acceptable in certain applications. Further, although driving circuit 70 is shown as comprising a pair of amplifiers, it will be apparent that a suitable single amplifier could be employed equally effective for driving individual segments 50 and 60. For example, each respective first end 52 and 62 could be readily connected in parallel to receive the output signal of a single amplifier, and thus, in this case, driving circuit 70, would only comprise a single amplifier. Thus, a transmission line, such as a center tapped transmission line, having respective segments electrically connected in parallel to a single amplifier can be optionally employed.

Individual segments 50 and 60 are preferably arranged so that respective first ends of any two consecutive segments are substantially adjacent to one another and respective second ends of any two consecutive segments are substantially adjacent to one another. The gap size between any two consecutive segments should be small relative to carrier wavelength. For example, about ⅛ in. for a 750 MHz carrier. This arrangement conveniently allows for avoiding time-delay discontinuities between any of the respective individual segments encircling the rotating frame. This allows for effective coupling operation between the transmission line and the coupler at all rotation angles. As shown in FIG. 2, each of the two individual segments 50 and 60 can be designed to subtend a respective angle of about 180° around the circumference of the rotating frame. In general, it will be appreciated that a number of N individual segments each respectively subtending an angle of about 360°/N around the rotating frame wherein N is a predetermined even number will be equally effective in alternative embodiments of the present invention since the modulated signal in each case is available for reception anywhere along the circumference of the rotating frame including any gaps between any of the N individual segments. The foregoing construction for the individual segments assumes that each segment is made up of a material having a substantially similar dielectric constant. However, it will be apparent that segment materials having predetermined different dielectric constants can also be conveniently employed. In this case, the angle subtended by each respective individual segment need not be identical to each other. As suggested above, there may be applications which can tolerate a predetermined time delay between respective first and second ends of the individual segments. In this case, the N number of individual segments need not be limited to an even number since a predetermined odd number of individual segments could be effectively utilized for applications which tolerate such predetermined time delay.

The apparatus of the present invention further comprises a coupler 100 attached to stationary frame 12 (FIG. 1) and being positioned sufficiently near the transmission line for establishing radio coupling therebetween in order to receive the modulated signal being applied to the respective individual segments. As used herein the expression "radio coupling" refers to noncontactive transfer of energy by electromagnetic radiation at radio frequencies.

It will be appreciated that coupler 100 has a predetermined length dimension along a coupler axis 102 which, for example, can be substantially parallel relative to individual segments 50 and 60. The coupler length dimension is conveniently chosen to be sufficiently short to avoid any substantial frequency-dependent directional coupling effects, and to be sufficiently long to avoid any substantial signal attenuation or reduction in coupler 100 whenever the coupler passes about any gap between respective ones of the individual segments. The expression "directional coupling effects" refers to effects which would cause the coupler to be sensitive only to a wave travelling in a particular direction while essentially "tuning out" a wave travelling in the opposite direction. As indicated by arrows 104 and 106, the modulated signal applied to respective segments 50 and 60 propagates in opposite directions and thus to avoid blind spots near any of the gaps, coupler 100 preferably has a first end 110 directly connected to output port means 112, such as a coaxial line or other suitably shielded electrical conductor, and has a second end 108 which is substantially free of any termination impedance, i.e., termination resistors. In this manner, the modulated signal received by coupler 100 passes to coaxial line 112 independently of the propagation direction of the received modulated signal, i.e., independently of the propagation direction of the electromagnetic wave traveling in individual segments 50 and 60. For instance, waves arriving at second end 108 readily propagate toward the first end and from there to coaxial line 112, whereas waves arriving at first end 110 are eventually reflected back from the resistively unterminated second end 108 toward the first end and from there to coaxial line 112. In each case, coupler 100 advantageously allows for non-contactively extracting the modulated signal in the transmission line along the full circumference of the rotating frame. An amplifier 114 can readily provide a predetermined amplification to the signal being supplied by coupler 100. As will be appreciated by those skilled in the art, the length dimension of the coupler can vary depending on the specific value of the carrier frequency being utilized for the modulated signal. By way of example and not of limitation, the coupler length dimension can be chosen in the range of $\lambda/4$ to $\lambda/8$ wherein $\lambda$ represents the wavelength of the carrier in the transmission line material. Other configurations for the coupler will be readily apparent to those skilled in the art. For example, a relatively short (e.g., about λ/16) center-tapped coupler can alternatively be employed in lieu of a coupler having a resistively unterminated end.

FIGS. 3A and 3B illustrate respective cross sections of substantially planar transmission lines which can be effectively used both for the transmission line segments and for the coupler. For example, FIG. 3A shows a microstrip 200 wherein a signal conductor 202 and a ground plane 206 are separated from one another by a suitable dielectric material 204. FIG. 3B shows a stripline 300 wherein a signal conductor 302 is "sandwiched" in a respective dielectric material 304 between two ground planes 308 and 306. It will be appreciated that any of the above-listed configuration can be readily fabricated employing well known printed circuit techniques which allow for substantial savings in cost as compared to an optical data link.

Figure 4B:
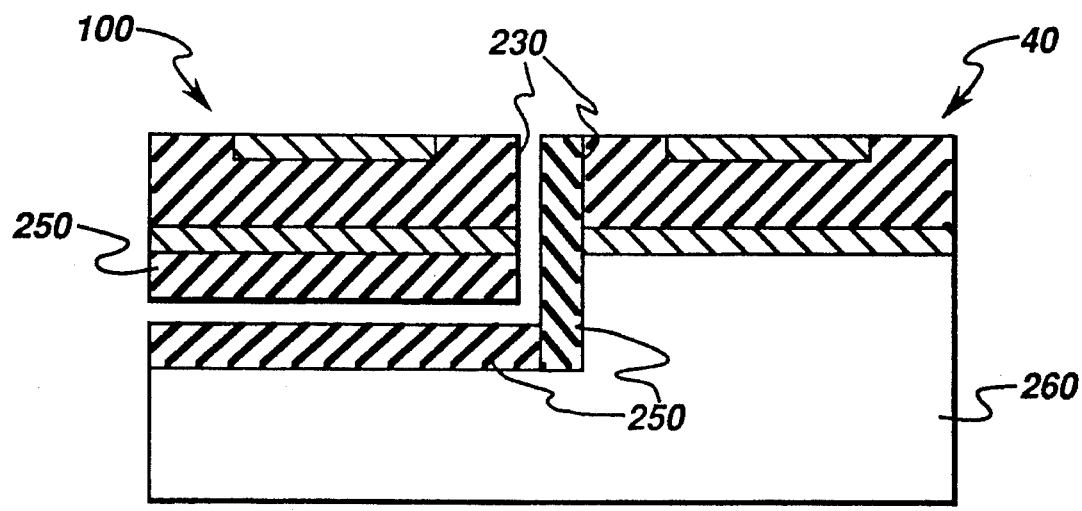
Figure 4C:
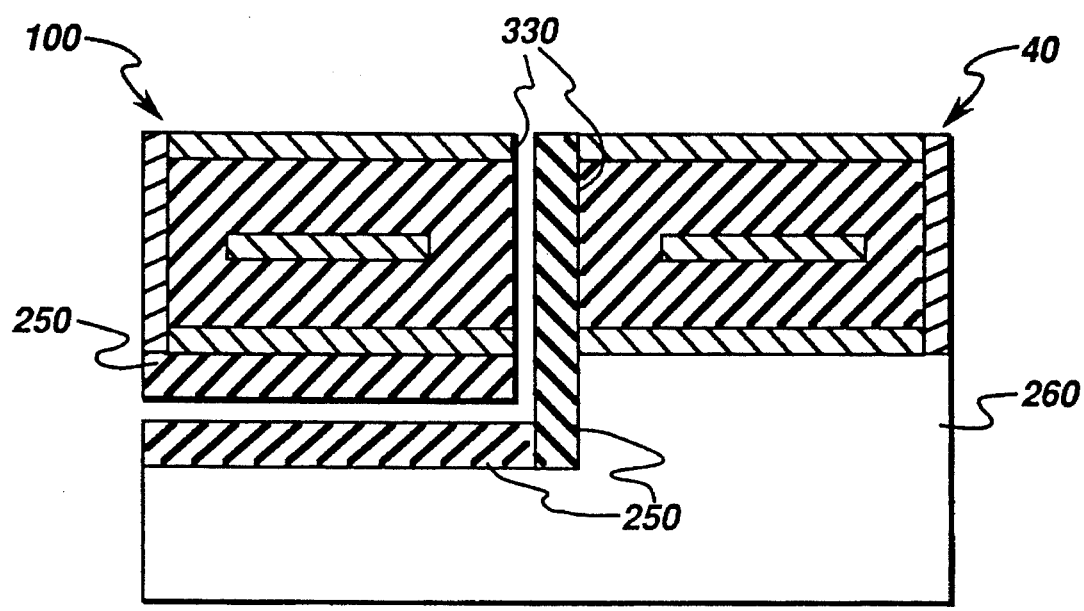

FIGS. 4A, 4B and 4C are respective cross-sectional views showing exemplary geometrical arrangements for the transmission line and coupler. FIG. 4A shows a respective microstrip arrangement for transmission line 40 and coupler 100. As shown in FIG. 4A, the transmission line and the coupler are situated with respect to one another so that, for example, a respective bottom surface 210 of coupler 100 substantially faces a top surface 220 of transmission line 40. It will be appreciated that the respective positioning for the coupler and transmission can easily be reversed with equally effective results. FIG. 4B, like FIG. 4A, also shows respective microstrip configurations for the transmission line and the coupler. In the arrangement of FIG. 4B, however, it is seen that predetermined lateral surfaces 230 substantially face one another instead of respective bottom and top surfaces. Further, both the transmission line and the coupler conveniently include slide means 250 made of a suitable low-friction material, such as Teflon polymer, in order to maintain a predetermined uniform spacing between the coupler and the transmission line. For example, a simple mechanical device, such as a spring and the like, can be employed for urging or pressing the, coupler against the transmission line as the rotating frame rotates to obtain image data. FIG. 4C shows respective stripline configurations geometrically arranged like the respective microstrips shown in FIG. 4B, i.e., both the transmission line and the coupler are situated so that predetermined lateral surfaces 330 substantially face one another. In each case, transmission line 40 can be constructed on a suitable substrate 260 that can be conveniently attached to the rotating frame by conventional means such as bonding, soldering, machining and the like. Further, transmission line 40, can be conveniently attached to the annulus surface of rotating frame 15, i.e., the surface bounded by the two concentric circles therein.

Figure 5:
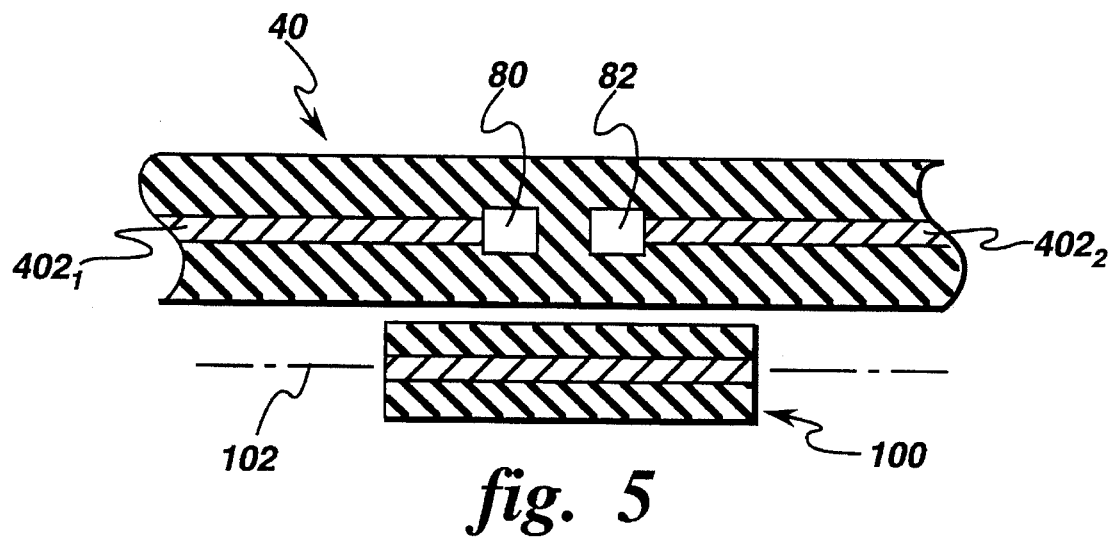
FIG. 5 is a generally schematic view showing further details of the apparatus of FIG. 2.

FIG. 5 shows one exemplary scheme for terminating the respective transmission line segments to minimize reflection of electromagnetic energy. As shown in FIG. 5, each of the individual transmission line segments has a respective signal conductor $402_1$ and $402_2$ each respectively connected to a predetermined electrical impedance, such as chip resistors 82 and 80 connected to the common ground plane for the microstrip or stripline transmission line segments. The straight connection for the termination resistors is preferred for the purpose of minimizing signal degradation at the termination points. Chip resistors 82 and 80 are preferably attached to the bottom (ground plane side) of the transmission lines and connected to the transmission line signal conductor via feed through connections so as to avoid mechanical interference as the coupler passes over any termination gap between the individual segments.

Figure 6:
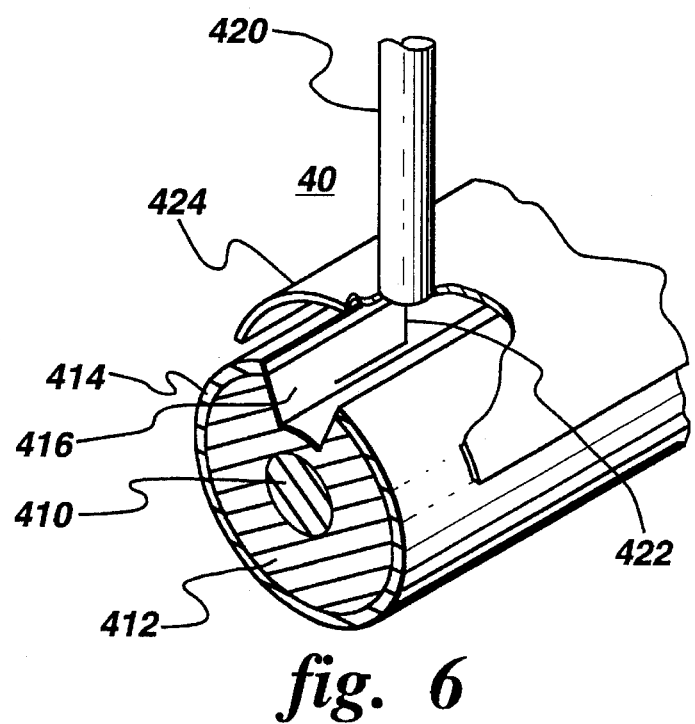
FIG. 6 is an isometric view of an exemplary alternate embodiment for the transmission line and coupler in accordance with the present invention.

FIG. 6 shows an alternative exemplary embodiment for transmission line 40. In this embodiment, the transmission line comprises a coaxial line made-up of a signal conductor 410 in a dielectric material 412 substantially surrounded by an outer conductor 414. As seen in FIG. 6, the coaxial line includes a notch 416 which conveniently receives coupler 100 (FIG. 2) for establishing the radio coupling for high data rate communication between the rotating and stationary frames. As shown in FIG. 6, coupler 100 may comprise a coaxial line 420 having a center conductor 422 and a shroud structure 424 which conveniently supports coupler 100 over notch 416. Thus it will be appreciated that, as described above, neither the coupler nor the transmission line need consist of a microstrip or a stripline transmission line.

A method for providing high data rate communication between the stationary and rotating frames of a CT system comprises the steps of attaching a transmission line comprising individual segments positioned around the rotating frame and having respective first and second ends. The transmission line may comprise a substantially planar transmission line configured, for example, as a microstrip transmission line or as a stripline transmission line. Alternatively, the transmission line can be made-up of a notched coaxial line. The electrical length of each of the individual segments is selected so that a modulated signal simultaneously applied at each respective first end has a predetermined time-delay upon arrival at each respective second end. The individual segments are arranged so that respective first end of any two consecutive segments are substantially adjacent to one another and respective second ends of any two consecutive segments are substantially adjacent to one another to avoid time-delay discontinuity in the modulated signal propagating therethrough. A coupler is attached to the stationary frame. The coupler is positioned sufficiently near the transmission line for establishing radio coupling therebetween so as to receive the modulating signal being applied to the respective individual segments. Additional steps may comprise connecting each respective second end of the respective individual segments to a predetermined electrical impedance, such as suitable termination resistors. The length dimension of the coupler, which typically is relatively short compared to the overall length of the transmission line, is selected to avoid directional coupling effects and/or signal attenuation in the coupler whenever the coupler passes about any gap between respective ones of the individual segments. The coupler and the transmission line can be mutually aligned with respect to one another so that predetermined lateral surfaces of the transmission line and the coupler substantially face one another. Alternatively, the coupler and the transmission line can be mutually aligned so that respective top and bottom surfaces of the transmission line and the coupler substantially face one another. In each case, the apparatus and method of the present invention advantageously allow for establishing reliable and low-cost high data rate communication between the rotating and stationary frames of a CT system.

Although various specific constructions have been given for the present invention, it is to be understood that these are for illustrative purposes only. Various modifications and adaptations will be readily apparent to those skilled in the art without departing from the substance or scope of the invention. For example, although the transmission line segments have been described as rotating along with rotating frame or gantry 15 (FIG. 1) and the coupler has been described as attached to stationary frame 12 (FIG. 1), it is equally possible to instead have the transmission line segments stationary and the coupler mounted on the rotating frame, i.e., stationary and rotating mechanical mounting for the coupler and transmission line segments can be readily interchanged with equally effective results. Accordingly, it is intended that the invention be limited only by the spirit and scope of the claims appended hereto.

What is claimed is:

1. In a computerized tomography system having a stationary frame and a generally annular rotating frame, an apparatus comprising:

a transmission line attached to said rotating frame and positioned substantially around said rotating frame, said transmission line comprising individual segments each having a respective first end and a respective second end, each of said individual segments having a respective electrical length chosen so that a modulated signal simultaneously applied at each respective first end has a predetermined time-delay upon arrival at each respective second end, said individual segments being arranged so that respective first ends of any two consecutive segments are substantially adjacent to one another and respective second ends of any two consecutive segments are substantially adjacent to one another to avoid time-delay discontinuity in the modulated signal propagating therethrough; and a coupler attached to said stationary frame and being sufficiently near said transmission line for establishing radio coupling therebetween so as to receive the modulated signal being applied to the respective individual segments.

2. The apparatus of claim 1 wherein said individual segments comprises at least two individual segments each respectively subtending a predetermined angle around said rotating frame.

3. The apparatus of claim 2 wherein each respective one of said at least two individual segments subtends an angle of about 180° around said rotating frame.

4. The apparatus of claim 1 wherein said individual segments comprises a number N of individual segments each respectively subtending a predetermined angle around said rotating frame.

5. The apparatus of claim 4 wherein the number N of individual segments is a predetermined even number.

6. The apparatus of claim 4 wherein each respective one of the N individual segments subtends an angle of about 360°/N around said rotating frame.

7. The apparatus of claim 4 wherein each of said individual segments comprises a coaxial transmission line having a respective notch for receiving said coupler along a circumference of said rotating frame.

8. The apparatus of claim 7 wherein said coupler comprises a coaxial transmission line.

9. The apparatus of claim 1 wherein each of said individual segments comprises a respective substantially planar transmission line.

10. The apparatus of claim 9 wherein each of said substantially planar transmission lines comprises a transmission line selected from the group consisting of microstrip and stripline transmission lines.

11. The apparatus of claim 9 wherein said coupler comprises a respective substantially planar transmission line having first and second opposite ends situated along a coupler axis aligned substantially parallel relative to said individual segments.

12. The apparatus of claim 11 wherein said coupler has a predetermined length dimension along said coupler axis sufficient to substantially avoid frequency-dependent directional coupling effects, and sufficient to avoid substantial signal reduction in said coupler whenever said coupler passes about any gap between respective ones of said individual segments.

13. The apparatus of claim 12 further comprising output port means coupled to said first end of said coupler for supplying the received modulated signal and wherein said second end of said coupler is substantially free of any termination impedance so that the modulated signal received by said coupler passes to said output port means independently of propogation direction of the received modulated signal.

14. The apparatus of claim 13 wherein the substantially planar transmission line for said coupler comprises a transmission line selected from the group consisting of microstrip and stripline transmission lines.

15. The apparatus of claim 11 wherein said coupler and said transmission line, respectively, have predetermined lateral surfaces substantially facing one another.

16. The apparatus of claim 11 wherein said coupler and said transmission line, respectively, have predetermined top and bottom surfaces substantially facing one another.

17. The apparatus of claim 9 further comprising driving means for simultaneously applying at each respective first end of said individual segments said modulated signal.

18. The apparatus of claim 17 wherein each respective second end of said individual segments is connected to a predetermined electrical impedance.

19. The apparatus of claim 1 wherein said coupler and said transmission line further include respective slide means for substantially maintaining a predetermined spacing between one another.

20. A computerized tomography system comprising:

a stationary frame;

a generally annular rotating frame;

a transmission line attached to said rotating frame and positioned substantially around said rotating frame, said transmission line comprising individual segments each having a respective first end and a respective second end, each of said individual segments having a respective electrical length chosen so that a modulated signal simultaneously applied at each respective first end has a predetermined time-delay upon arrival at each respective second end, said individual segments being arranged so that respective first ends of any two consecutive segments are substantially adjacent to one another and respective second ends of any two consecutive segments are substantially adjacent to one another to avoid time-delay discontinuity in the modulated signal propagating therethrough; and a coupler attached to said stationary frame and being sufficiently near said transmission line for establishing radio coupling therebetween so as to receive the modulated signal being applied to the respective individual segments.

21. The computerized tomography system of claim 20 wherein said individual segments comprises at least two individual segments each respectively subtending a predetermined angle around said rotating frame.

22. The computerized tomography system of claim 21 wherein each respective one of said at least two individual segments subtends an angle of about 180° around said rotating frame.

23. The computerized tomography system of claim 20 wherein said individual segments comprises a number N of individual segments each respectively subtending a predetermined angle around said rotating frame.

24. The computerized tomography system of claim 23 wherein the number N of individual segments is a predetermined even number.

25. The computerized tomography system of claim 23 wherein each respective one of the N individual segments subtends an angle of about 360°/N around said rotating frame.

26. The computerized tomography system of claim 23 wherein each of said individual segments comprises a coaxial transmission line having a respective notch for receiving said coupler along a circumference of said rotating frame.

27. The computerized tomography system of claim 26 wherein said coupler comprises a coaxial transmission line.

28. The computerized tomography system of claim 20 wherein each of said individual segments comprises a respective substantially planar transmission line.

29. The computerized tomography system of claim 28 wherein each of said substantially planar transmission lines comprises a transmission line selected from the group consisting of microstrip and stripline transmission lines.

30. The computerized tomography system of claim 28 wherein said coupler comprises a respective substantially planar transmission line having first and second opposite ends situated along a coupler axis aligned substantially parallel relative to said individual segments.

31. The computerized tomography system of claim 30 wherein said coupler has a predetermined length dimension along said coupler axis sufficient to substantially avoid frequency-dependent directional coupling effects, and sufficient to avoid substantial signal reduction in said coupler whenever said coupler passes about any gap between respective ones of said individual segments.

32. The computerized tomography system of claim 31 further comprising output port means coupled to said first end of said coupler for supplying the received modulated signal and wherein said second end of said coupler is substantially free of any termination impedance so that the modulated signal received by said coupler passes to said output port means independently of propogation direction of the received modulated signal.

33. The computerized tomography system of claim 32 wherein the substantially planar transmission line for said coupler comprises a transmission line selected from the group consisting of microstrip and stripline transmission lines.

34. The computerized tomography system of claim 30 wherein said coupler and said transmission line, respectively, have predetermined lateral surfaces substantially facing one another.

35. The computerized tomography system of claim 30 Wherein said coupler and said transmission line, respectively, have predetermined top and bottom surfaces substantially facing one another.

36. The computerized tomography system of claim 28 further comprising driving means for simultaneously applying at each respective first end of said individual segments said modulated signal.

37. The computerized tomography system of claim 36 wherein each respective second end of said individual segments is connected to a predetermined electrical impedance.

38. The computerized tomography system of claim 20 wherein said coupler and said transmission line further include respective slide means for substantially maintaining a predetermined spacing between one another.

39. In a computerized tomography system having a rotating frame and a generally stationary frame, an apparatus comprising:

a transmission line attached to said generally stationary frame, said transmission line comprising individual segments each having a respective first end and a respective second end, each of said individual segments having a respective electrical length chosen so that a respective modulated signal simultaneously applied at each respective first end has a substantially similar time-delay relative to one another upon arrival at each respective second end, said individual segments being arranged so that respective first ends of any two consecutive segments are substantially adjacent to one another and respective second ends of any two consecutive segments are substantially adjacent to one another to avoid time-delay discontinuity in the modulated signal propagating therethrough; and a coupler attached to said rotating frame and being sufficiently near said transmission line for establishing radio coupling therebetween so as to receive the modulated signal being applied to the respective individual segments.

40. A method for providing high data rate communication between a stationary frame and a rotating frame, said method comprising the steps of:

attaching a transmission line comprising individual segments to said rotating frame, each individual segment having respective first and second ends;

selecting the electrical length of each of the individual segments so that a modulated signal simultaneously applied at each respective first end has a predetermined time-delay upon arrival at each respective second end;

arranging the individual segments so that respective first ends of any two consecutive segments are substantially adjacent to one another and respective second ends of any two consecutive segments are substantially adjacent to one another to avoid time-delay discontinuity in the modulated signal propagating therethrough;

attaching a coupler to the stationary frame; and positioning the coupler sufficiently near the transmission line for establishing radio coupling therebetween so as to receive the modulating signal being applied to the respective individual segments.

41. The method of claim 40 further comprising the step of connecting each respective second end of said individual segments to a predetermined electrical impedance.

42. The method of claim 41 further comprising the step of selecting a predetermined coupler length dimension which is sufficient to avoid frequency-dependent directional coupling effects, and sufficient to avoid signal reduction in the coupler whenever the coupler passes about any gap between respective ones of the individual segments.

43. The method of claim 42 further comprising the step of mutually aligning the transmission line and the coupler so that predetermined lateral surfaces of said transmission line and said coupler substantially face one another.

44. The method of claim 42 further comprising the step of mutually aligning the transmission line and the coupler so that respective top and bottom surfaces of said transmission line and said coupler substantially face one another.

* * * * *

UNITED STATES PATENT AND TRADEMARK OFFICE
CERTIFICATE OF CORRECTION

PATENT NO. : 5,530,424
DATED : June 25, 1996
INVENTOR(S) : Daniel D. Harrison and Richard L. Frey It is certified that error appears in the above-indentified patent and that said Letters Patent is hereby corrected as shown below:

On the title page, item [45], delete "*"; and under item [73], delete "[*] Notice: The term of this patent shall not extend beyond the expiration date of Pat. No. 5,530,7220."

Signed and Sealed this

Twenty-first Day of January, 1997

Attest:

BRUCE LEHMAN

*Attesting Officer*    *Commissioner of Patents and Trademarks*